United States Patent
Wiedemann

(10) Patent No.: US 12,247,034 B1
(45) Date of Patent: Mar. 11, 2025

(54) CRYSTALLINE FORM OF DEURUXOLITINIB PHOSPHATE

(71) Applicant: Sun Pharmaceutical Industries, Inc., Princeton, NJ (US)

(72) Inventor: Sean Wiedemann, Burlington, MA (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 0 days.

(21) Appl. No.: 18/661,225

(22) Filed: May 10, 2024

Related U.S. Application Data

(60) Provisional application No. 63/636,516, filed on Apr. 19, 2024.

(51) Int. Cl.
*A61K 31/519* (2006.01)
*C07D 487/04* (2006.01)

(52) U.S. Cl.
CPC .......... *C07D 487/04* (2013.01); *A61K 31/519* (2013.01)

(58) Field of Classification Search
CPC .......................... A61K 31/519; C07D 487/04
USPC ........................................ 514/265.1; 544/253
See application file for complete search history.

(56) References Cited

U.S. PATENT DOCUMENTS

| 10,561,659 B2 | 2/2020 | Wagner et al. |
| 2008/0312259 A1 | 12/2008 | Rodgers et al. |
| 2022/0213105 A1 | 7/2022 | Lewis et al. |
| 2023/0286953 A1 | 9/2023 | Bazinet et al. |
| 2023/0355629 A1 | 11/2023 | Silverman et al. |

FOREIGN PATENT DOCUMENTS

| CA | 2928286 A1 | 10/2016 |
| IN | 202041013253 | 10/2021 |
| WO | 2016/063294 A2 | 4/2016 |
| WO | 2020/163653 A1 | 8/2020 |
| WO | 2022/036030 A1 | 2/2022 |

OTHER PUBLICATIONS

Declaration under 37 C.F.R. 1.132 of James D. Rogers in U.S. Appl. No. 12/137,892, filed Jun. 7, 2010.

*Primary Examiner* — Douglas M Willis
(74) *Attorney, Agent, or Firm* — MEDLER FERRO WOODHOUSE & MILLS PLLC

(57) ABSTRACT

The present disclosure is directed to polymorph Form 1 of 1H-pyrazole-1-propanenitrile, β-(cyclopentyl-2,2,3,3,4,4,5,5-$d_8$)-4-(7H-pyrrolo[2,3-*d*]pyrimidin-4-*yl*)-, (βR)-, phosphate (1:1) (deuruxolitinib phosphate). Also disclosed are methods of treatment using polymorph Form 1 of deuruxolitinib phosphate and methods of making polymorph Form 1 of deuruxolitinib phosphate.

14 Claims, 4 Drawing Sheets

CRYSTALLINE FORM OF DEURUXOLITINIB PHOSPHATE

FIELD OF THE INVENTION

The present disclosure is directed to polymorph Form 1 of 1H-pyrazole-1-propanenitrile, β-(cyclopentyl-2,2,3,3,4,4,5,5-$d_8$)-4-(7H-pyrrolo[2,3-d]pyrimidin-4-yl)-, (βR)-, phosphate (1:1) (deuruxolitinib phosphate). Also disclosed are methods of treatment using polymorph Form 1 of deuruxolitinib phosphate and methods of making polymorph Form 1 of deuruxolitinib phosphate.

BACKGROUND OF THE INVENTION

Deuruxolitinib phosphate, known by the chemical name 1H-pyrazole-1-propanenitrile, β-(cyclopentyl-2,2,3,3,4,4,5,5-$d_8$)-4-(7H-pyrrolo[2,3-d]pyrimidin-4-yl)-, (βR)-, phosphate (1:1), is a Janus kinase (JAK) inhibitor. U.S. Pat. No. 10,561,659 reports the use of deuruxolitinib phosphate for the treatment of hair loss disorders. PCT publication Nos. WO2020163653 and WO/2022/036030 reports processes for the preparation of deuruxolitinib.

Often, a given active agent can exist in an amorphous form, or in a mixture of amorphous form and crystalline form. A polymorphic form can exist in some active agents. Polymorphic forms can occur where the active agent crystallizes in a specific lattice arrangement. In some instances, an active agent can form two or more different polymorphic forms. In some embodiments, each polymorphic form results in a different thermodynamic property, stability property, pharmacokinetic property, or other desirable properties.

SUMMARY OF THE INVENTION

The disclosure is directed to a polymorph of 1H-pyrazole-1-propanenitrile, β-(cyclopentyl-2,2,3,3,4,4,5,5-$d_8$)-4-(7H-pyrrolo[2,3-d]pyrimidin-4-yl)-, (βR)-, phosphate (1:1), wherein the polymorph is Form 1 comprising a powder X-ray diffraction pattern (XPRD) comprising three or more peaks expressed in degrees 2-theta selected from 4.03±0.2, 14.54±0.2, 24.95±0.2, and 25.29±0.2 degrees. In some embodiments, the XPRD comprises peaks expressed in degrees 2-theta at each of 4.03±0.2, 14.54±0.2, 24.95±0.2, and 25.29±0.2 degrees.

In some embodiments, the XPRD further of polymorph Form 1 comprises at least one additional peak expressed in degrees 2-theta selected from 14.77, 20.87, 21.76, and 26.36. In some embodiments, the XPRD further comprises at least two additional peaks expressed in degrees 2-theta selected from 14.77±0.2, 20.87±0.2, 21.76±0.2, and 26.36±0.2. In some embodiments, the XPRD further comprises at least three additional peaks expressed in degrees 2-theta selected from 14.77±0.2, 20.87±0.2, 21.76±0.2, and 26.36±0.2. In some embodiments, the XPRD further comprises at least four additional peaks expressed in degrees 2-theta at each of 14.77±0.2, 20.87±0.2, 21.76±0.2, and 26.36±0.2.

In some embodiments, the XPRD of polymorph Form 1 further comprises at least one additional peak expressed in degrees 2-theta selected from 7.55±0.2, 8.36±0.2, 15.94±0.2, and 20.41±0.2. In some embodiments, the XPRD further comprises at least two additional peaks expressed in degrees 2-theta selected from 7.55±0.2, 8.36±0.2, 15.94±0.2, and 20.41±0.2. In some embodiments, the XPRD further comprises at least three additional peaks expressed in degrees 2-theta selected from 7.55±0.2, 8.36±0.2, 15.94±0.2, and 20.41±0.2.

In some embodiments, polymorph Form 1 has an XRPD pattern substantially as shown in FIG. 1.

In some embodiments, polymorph Form 1 is further characterized by one or more of: (a) a DSC spectrum (10° C./min) comprising an endotherm onset at 194.3±1.0° C. and peak at 197.4±1.0° C.; (b) an FT-Raman spectrum substantially as depicted in FIG. 3; and (c) a TG-FTIR thermogram substantially as depicted in FIG. 4.

In some embodiments, the polymorph Form 1 has at least 90% deuterium incorporation at each of the specified deuterated positions, as determined by $^1$H-NMR. In some embodiments, the polymorph Form 1 has at least 95% deuterium incorporation at each of the specified deuterated positions, as determined by $^1$H-NMR.

In some embodiments, the polymorph Form 1 is substantially free of 1H-pyrazole-1-propanenitrile, β-(cyclopentyl-2,2,3,3,4,4,5,5-$d_8$)-4-(7H-pyrrolo[2,3-d]pyrimidin-4-yl)-, (βS)-, phosphate (1:1) as determined by $^1$H-NMR. In some embodiments, the polymorph Form 1 is substantially free of amorphous 1H-pyrazole-1-propanenitrile, β-(cyclopentyl-2,2,3,3,4,4,5,5-$d_8$)-4-(7H-pyrrolo[2,3-d]pyrimidin-4-yl)-, (βR)-, phosphate (1:1).

In some embodiments, the polymorph Form 1 is substantially anhydrous. In some embodiments, the polymorph is substantially crystalline.

In some embodiments, the disclosure provides a pharmaceutical composition comprising the polymorph Form 1 as described herein, and a pharmaceutically acceptable carrier. In some embodiments, the ratio of the amount of Form 1 polymorph to the sum of the amounts of other polymorphic forms in the pharmaceutical composition is at least 90:10 (wt/wt).

In some embodiments, the ratio of the amount of Form 1 polymorph in the pharmaceutical composition to the sum of the amounts of other polymorphic forms is at least 95:5. In some embodiments, the ratio of the amount of Form 1 polymorph in the pharmaceutical composition to the sum of the amounts of other polymorphic forms is at least 99:1.

In some embodiments, the disclosure provides a method of treating a disease, disorder or condition mediated alone, or in part, by Janus Associated Kinases (JAKs) in a patient comprising the step of administering to the patient a polymorph of Form 1 as described herein, or a pharmaceutical composition comprising polymorph Form 1 as described herein.

In some embodiments, the disclosure provides a process for the preparation of the polymorph Form 1 as described herein, comprising (i) forming a slurry of 1H-pyrazole-1-propanenitrile, β-(cyclopentyl-2,2,3,3,4,4,5,5-$d_8$)-4-(7H-pyrrolo[2,3-d]pyrimidin-4-yl)-, (βR)-, phosphate (1:1) in isopropanol or an isopropanol/water mixture, and (ii) isolating Form 1 of deuruxolitinib phosphate from the slurry, e.g., by filtration. In some embodiments, the slurry is formed in an isopropanol/water mixture at a ratio of about 80:20 to about 99:1, or a ratio of about 80:20 to about 98:2. In some embodiments, the slurry is formed in an isopropanol/water mixture at a ratio of about 90:10.

DETAILED DESCRIPTION OF THE INVENTION

Figure 1:
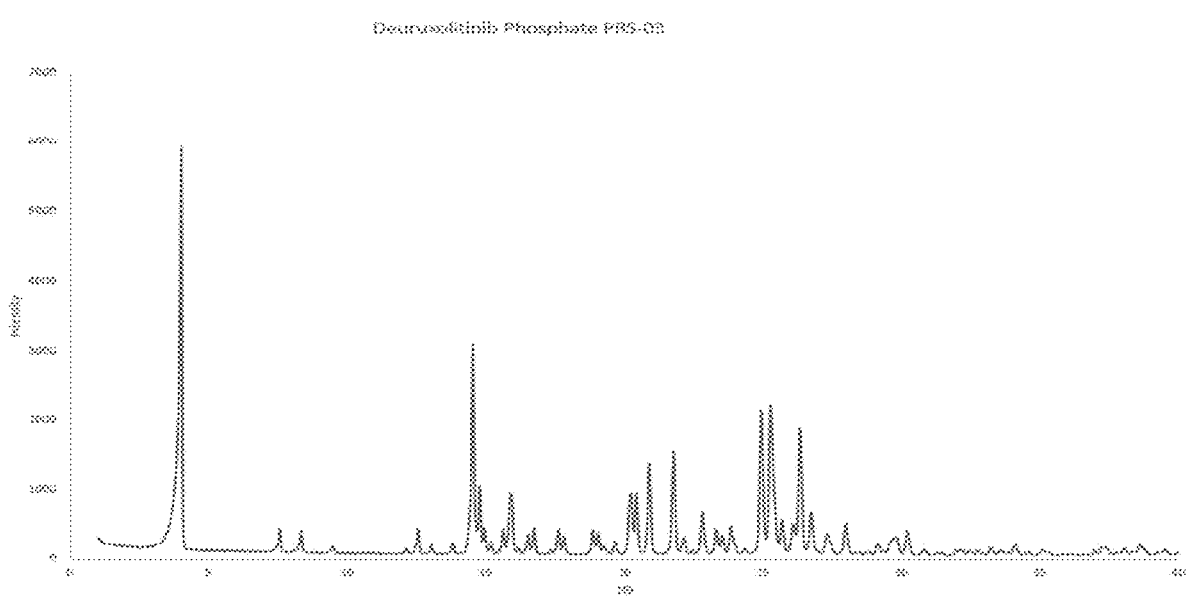
FIG. 1 depicts the normalized X-ray powder diffraction (XRPD) of Form 1 of deuruxolitinib phosphate (1:1).

The present disclosure relates to polymorphic forms of 1H-pyrazole-1-propanenitrile, β-(cyclopentyl-2,2,3,3,4,4,5,5-d$_8$)-4-(7H-pyrrolo[2,3-d]pyrimidin-4-yl)-, (βR)-, phosphate (1:1) (deuruxolitinib phosphate), methods making deuruxolitinib phosphate, pharmaceutical compositions comprising deuruxolitinib phosphate and the use of deuruxolitinib phosphate for treating, preventing, or ameliorating a disease or condition comprising administering a polymorph of the invention.

The term 1H-pyrazole-1-propanenitrile, β-(cyclopentyl-2,2,3,3,4,4,5,5-d$_8$)-4-(7H-pyrrolo[2,3-d]pyrimidin-4-yl)-, (βR)-, phosphate (1:1) can be represented by a compound of Formula I:

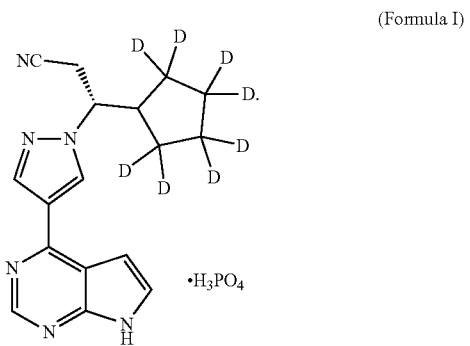

(Formula I)

1H-pyrazole-1-propanenitrile, β-(cyclopentyl-2,2,3,3,4,4,5,5-d$_8$)-4-(7H-pyrrolo[2,3-d]pyrimidin-4-yl)-, (βR)-, phosphate (1:1) is also interchangeably referred to herein as deuruxolitinib phosphate and deuruxolitinib phosphate (1:1). One of skill in the art will understand that for each of the positions shown in Formula I as deuterium (i.e., "D"), deuterium may not be incorporated in 100% of the positions and would still fall within the scope of the term deuruxolitinib phosphate. In some embodiments, the term "deuruxolitinib phosphate" refers to a material in which given a population of deuruxolitinib phosphate molecules, e.g., a preparation of deuruxolitinib phosphate, at least 90% of each specified deuterated position comprises deuterium, or at least 91%, at least 92%, at least 93%, at least 94%, at least 95%, at least 96%, at least 97%, at least 98%, or at least 99% of each specified deuterated position comprises deuterium as determined by $^1$H-NMR.

In some embodiments, the disclosure is directed to Form 1 of 1H-pyrazole-1-propanenitrile, β-(cyclopentyl-2,2,3,3,4,4,5,5-d$_8$)-4-(7H-pyrrolo[2,3-d]pyrimidin-4-yl)-, (βR)-, phosphate. The term "Form 1 of 1H-pyrazole-1-propanenitrile, β-(cyclopentyl-2,2,3,3,4,4,5,5-ds)-4-(7H-pyrrolo[2,3-d]pyrimidin-4-yl)-, (βR)-, phosphate" can be used interchangeably herewith with the terms "Form 1 of 1H-pyrazole-1-propanenitrile, β-(cyclopentyl-2,2,3,3,4,4,5,5-ds)-4-(7H-pyrrolo[2,3-d]pyrimidin-4-yl)-, (βR)-, phosphate (1:1)," "Form 1 of deuruxolitinib phosphate," "Form 1 of deuruxolitinib phosphate (1:1)," "Form 1," "deuruxolitinib phosphate Form 1", "deuruxolitinib phosphate polymorph Form I" and "the Form 1 polymorph."

When the term "1H-pyrazole-1-propanenitrile, β-(cyclopentyl-2,2,3,3,4,4,5,5-d$_8$)-4-(7H-pyrrolo[2,3-d]pyrimidin-4-yl)-, (βR)-, phosphate" or "deuruxolitinib phosphate" is used without specifying the crystalline form, this term refers to the compound in any form, such as crystalline, amorphous, or other, or in a combination of forms.

Different polymorphic forms of a given compound, e.g., deuruxolitinib phosphate, may have different properties, such as solubility, dissolution rate, suspension stability, stability during milling, vapor pressure, optical and mechanical properties, hygroscopicity, crystal size, filtration performance, drying, density, melting point, degradation stability, stability to prevent phase change to other forms, color and even chemical reactivity. More importantly, in some embodiments, the different forms of a small molecule compound such as deuruxolitinib phosphate can change its dissolution, dissolution performance, pharmacokinetics and bioavailability, which can, in some instances, affect the efficacy and safety performance of the compound.

In particular, in some embodiments, crystal forms of deuruxolitinib phosphate, e.g., deuruxolitinib phosphate Form 1, can affect its dissolution, absorption in vivo, thereby affecting its clinical therapeutic effect and safety to a certain extent. In some embodiments, crystal forms of deuruxolitinib phosphate can be critical for drug quality control. The present disclosure relates to deuruxolitinib phosphate Form 1 and compositions and kits thereof, methods of making deuruxolitinib phosphate Form 1, and methods of treating, preventing, or ameliorating a disease, disorder, or condition by administering a therapeutically effective amount of deuruxolitinib phosphate Form 1.

The present disclosure provides a new polymorphic form of deuruxolitinib phosphate, Form 1. In some embodiments, the deuruxolitinib phosphate Form 1 is an anhydrous, non-solvated crystalline form. The present application describes the chemical and physical characteristics of this polymorphic form, and discloses methods for making this polymorph form.

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular. As used herein, "a" or "an" may mean one or more. As used herein, when used in conjunction with the word "comprising," the words "a" or "an" may mean one or more than one. As used herein, "another" or "a further" may mean at least a second or more.

Throughout this application, the term "about" is used to indicate that a value includes the inherent variation of error for the method/device being employed to determine the value, or the variation that exists among the study subjects. Typically, the term "about" is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability, depending on the situation.

The use of the term "or" in the claims is used to mean "and/or", unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps. It is contemplated that any embodiment discussed in this specification can be implemented with respect to polymorph, methods, and/or kits of the present disclosure. Furthermore, the polymorph and/or kits of the present disclosure can be used to achieve the methods of the present disclosure.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

As used herein, the term "room temperature" generally refers to 4° C. to 30° C., 18° C. to 22° C., 19° C. to 21° C. or 20±5° C.

Form 1 can be described by one or more solid state analytical methods, for example, by its powder X-ray diffraction pattern, differential scanning calorimetry (DSC), FT-Raman spectroscopy and/or thermogravimetric measurements.

In some embodiments, the Form 1 can be determined by its X-ray diffraction pattern (XRPD) as measured by 2θ. For a characteristic diffraction peak represented by a 2 theta (2q) angle, the term "about" means that the listed value varies by no more than ±0.2°, for example, about X°, it means X±±0.2°, preferably X±0.1°. Thus, in some embodiments, any of the 2q angle recited herein can be ±0.1.

The disclosure herein provides deuruxolitinib phosphate Form 1. In some embodiments, the deuruxolitinib phosphate Form 1 comprises a powder X-ray diffraction pattern (XPRD) comprising three or more peaks expressed in degrees 2-theta selected from 4.03±0.2, 14.54±0.2, 24.95±0.2, and 25.29±0.2 degrees.

In some embodiments, deuruxolitinib phosphate Form 1 comprises peaks at least at 4.03±0.2, 14.54±0.2 and 24.95±0.2 degrees 2-theta. In some embodiments, deuruxolitinib phosphate Form 1 comprises peaks at least at 4.03±0.2, 14.54±0.2, and 25.29±0.2 degrees 2-theta. In some embodiments, deuruxolitinib phosphate Form 1 comprises peaks at least at 4.03±0.2, 24.95±0.2, and 25.29±0.2 degrees 2-theta. In some embodiments, deuruxolitinib phosphate Form 1 comprises peaks at least at 14.54±0.2, 24.95±0.2, and 25.29±0.2 degrees 2-theta. In some embodiments, deuruxolitinib phosphate Form 1 comprises peaks expressed in degrees 2-theta at each of 4.03±0.2, 14.54±0.2, 24.95±0.2, and 25.29±0.2 degrees.

In some embodiments, the deuruxolitinib phosphate polymorph Form I comprises three or more peaks expressed in degrees 2-theta selected from 4.03±0.2, 14.54±0.2, 24.95±0.2, and 25.29±0.2 degrees, and further comprises at least one additional peak expressed in degrees 2-theta selected from 14.77±0.2, 20.87±0.2, 21.76±0.2, and 26.36±0.2. In some embodiments, deuruxolitinib phosphate polymorph Form I comprises three or more peaks expressed in degrees 2-theta selected from 4.03±0.2, 14.54±0.2, 24.95±0.2, and 25.29±0.2 degrees, and further comprises at least two additional peaks expressed in degrees 2-theta selected from 14.77±0.2, 20.87±0.2, 21.76±0.2, and 26.36±0.2. In some embodiments, deuruxolitinib phosphate polymorph Form I comprises three or more peaks expressed in degrees 2-theta selected from 4.03±0.2, 14.54±0.2, 24.95±0.2, and 25.29±0.2 degrees, and further comprises at least three additional peaks expressed in degrees 2-theta selected from 14.77±0.2, 20.87±0.2, 21.76±0.2, and 26.36±0.2. In some embodiments, deuruxolitinib phosphate polymorph Form I comprises three or more peaks expressed in degrees 2-theta selected from 4.03±0.2, 14.54±0.2, 24.95±0.2, and 25.29±0.2 degrees, and further comprises at least four additional peaks expressed in degrees 2-theta at each of 14.77±0.2, 20.87±0.2, 21.76±0.2, and 26.36±0.2.

In some embodiments, the deuruxolitinib phosphate polymorph Form I further comprises at least one additional peak expressed in degrees 2-theta selected from 7.55±0.2, 8.36±0.2, 15.94±0.2, and 20.41±0.2. In some embodiments, the deuruxolitinib phosphate polymorph Form I further comprises at least two additional peaks expressed in degrees 2-theta selected from 7.55±0.2, 8.36±0.2, 15.94±0.2, and 20.41±0.2. In some embodiments, the deuruxolitinib phosphate polymorph Form I further comprises at least three additional peaks expressed in degrees 2-theta selected from 7.55±0.2, 8.36±0.2, 15.94±0.2, and 20.41±0.2. In some embodiments, the deuruxolitinib phosphate polymorph Form I further comprises four additional peaks expressed in degrees 2-theta at 7.55±0.2, 8.36°±0.2, 15.94±0.2, and 20.41±0.2.

In some embodiments, deuruxolitinib phosphate polymorph Form I comprises three or more peaks expressed in degrees 2-theta selected from 4.03±0.2, 14.54±0.2, 24.95±0.2, and 25.29±0.2 degrees, and further comprises at least two additional peaks expressed in degrees 2-theta selected from 7.55±0.2, 8.36°±0.2, 15.94±0.2, and 20.41±0.2. In some embodiments, deuruxolitinib phosphate polymorph Form I comprises three or more peaks expressed in degrees 2-theta selected from 4.03±0.2, 14.54±0.2, 24.95±0.2, and 25.29±0.2 degrees, and further comprises at least three additional peaks expressed in degrees 2-theta selected from 7.55±0.2, 8.36°±0.2, 15.94±0.2, and 20.41±0.2.

In some embodiments, deuruxolitinib phosphate polymorph Form I comprises the peaks expressed in degrees 2-theta as found in one of (i) Table 2, Column A, (ii) Table 2, Column A and one of Column B, or (iii) Table 2, Column A and one of Column B and one or more peaks from Column C, e.g., one peak, two peaks, three peaks or four peaks from Column C.

TABLE 2

| Colum A | Column B | Column C |
| --- | --- | --- |
| 4.03 ± 0.2, | 14.77 ± 0.2, | 7.55 ± 0.2, |
| 14.54 ± 0.2, | 20.87 ± 0.2, | 8.36 ± 0.2, |
| 24.95 ± 0.2, | 21.76 ± 0.2, | 15.94 ± 0.2, |
|  | 26.36 ± 0.2 | 20.41 ± 0.2 |
|  | 14.77 ± 0.2, 20.87 ± 0.2, |  |
|  | 14.77 ± 0.2, 21.76 ± 0.2, |  |
|  | 14.77 ± 0.2, 26.36 ± 0.2 |  |

TABLE 2-continued

| Colum A | Column B | Column C |
|---|---|---|
| | 20.87 ± 0.2, 21.76 ± 0.2, | |
| | 20.87 ± 0.2, 26.36 ± 0.2 | |
| | 21.76 ± 0.2, 26.36 ± 0.2 | |
| | 14.77 ± 0.2, 20.87 ± 0.2, 21.76 ± 0.2, | |
| | 14.77 ± 0.2, 20.87 ± 0.2, 26.36 ± 0.2 | |
| | 14.77 ± 0.2, 21.76 ± 0.2, 26.36 ± 0.2 | |
| | 20.87 ± 0.2, 21.76 ± 0.2, 26.36 ± 0.2 | |
| | 14.77 ± 0.2, 20.87 ± 0.2, 21.76 ± 0.2, 26.36 ± 0.2 | |
| 4.03 ± 0.2, 14.54 ± 0.2, 25.29 ± 0.2 | 14.77 ± 0.2, 20.87 ± 0.2, 21.76 ± 0.2, 26.36 ± 0.2 | 7.55 ± 0.2, 8.36 ± 0.2, 15.94 ± 0.2, 20.41 ± 0.2 |
| | 14.77 ± 0.2, 20.87 ± 0.2, | |
| | 14.77 ± 0.2, 21.76 ± 0.2, | |
| | 14.77 ± 0.2, 26.36 ± 0.2 | |
| | 20.87 ± 0.2, 21.76 ± 0.2, | |
| | 20.87 ± 0.2, 26.36 ± 0.2 | |
| | 21.76 ± 0.2, 26.36 ± 0.2 | |
| | 14.77 ± 0.2, 20.87 ± 0.2, 21.76 ± 0.2, | |
| | 14.77 ± 0.2, 20.87 ± 0.2, 26.36 ± 0.2 | |
| | 14.77 ± 0.2, 21.76 ± 0.2, 26.36 ± 0.2 | |
| | 20.87 ± 0.2, 21.76 ± 0.2, 26.36 ± 0.2 | |
| | 14.77 ± 0.2, 20.87 ± 0.2, 21.76 ± 0.2, 26.36 ± 0.2 | |
| 4.03 ± 0.2, 24.95 ± 0.2, 25.29 ± 0.2 | 14.77 ± 0.2, 20.87 ± 0.2, 21.76 ± 0.2, 26.36 ± 0.2 | 7.55 ± 0.2, 8.36 ± 0.2, 15.94 ± 0.2, 20.41 ± 0.2 |
| | 14.77 ± 0.2, 20.87 ± 0.2, | |
| | 14.77 ± 0.2, 21.76 ± 0.2, | |
| | 14.77 ± 0.2, 26.36 ± 0.2 | |
| | 20.87 ± 0.2, 21.76 ± 0.2, | |
| | 20.87 ± 0.2, 26.36 ± 0.2 | |
| | 21.76 ± 0.2, 26.36 ± 0.2 | |
| | 14.77 ± 0.2, 20.87 ± 0.2, 21.76 ± 0.2, | |
| | 14.77 ± 0.2, 20.87 ± 0.2, 26.36 ± 0.2 | |
| | 14.77 ± 0.2, 21.76 ± 0.2, 26.36 ± 0.2 | |
| | 20.87 ± 0.2, 21.76 ± 0.2, 26.36 ± 0.2 | |
| | 14.77 ± 0.2, 20.87 ± 0.2, 21.76 ± 0.2, 26.36 ± 0.2 | |
| 14.54 ± 0.2, 24.95 ± 0.2, 25.29 ± 0.2 | 14.77 ± 0.2, 20.87 ± 0.2, 21.76 ± 0.2, 26.36 ± 0.2 | 7.55 ± 0.2, 8.36 ± 0.2, 15.94 ± 0.2, 20.41 ± 0.2 |
| | 14.77 ± 0.2, 20.87 ± 0.2, | |
| | 14.77 ± 0.2, 21.76 ± 0.2, | |
| | 14.77 ± 0.2, 26.36 ± 0.2 | |
| | 20.87 ± 0.2, 21.76 ± 0.2, | |
| | 20.87 ± 0.2, 26.36 ± 0.2 | |
| | 21.76 ± 0.2, 26.36 ± 0.2 | |
| | 14.77 ± 0.2, 20.87 ± 0.2, 21.76 ± 0.2, | |
| | 14.77 ± 0.2, 20.87 ± 0.2, 26.36 ± 0.2 | |
| | 14.77 ± 0.2, 21.76 ± 0.2, 26.36 ± 0.2 | |
| | 20.87 ± 0.2, 21.76 ± 0.2, 26.36 ± 0.2 | |
| | 14.77 ± 0.2, 20.87 ± 0.2, 21.76 ± 0.2, 26.36 ± 0.2 | |
| 4.03 ± 0.2, 14.54 ± 0.2, 24.95 ± 0.2, 25.29 ± 0.2 | 14.77 ± 0.2, 20.87 ± 0.2, 21.76 ± 0.2, 26.36 ± 0.2 | 7.55 ± 0.2, 8.36 ± 0.2, 15.94 ± 0.2, 20.41 ± 0.2 |
| | 14.77 ± 0.2, 20.87 ± 0.2, | |
| | 14.77 ± 0.2, 21.76 ± 0.2, | |
| | 14.77 ± 0.2, 26.36 ± 0.2 | |
| | 20.87 ± 0.2, 21.76 ± 0.2, | |
| | 20.87 ± 0.2, 26.36 ± 0.2 | |
| | 21.76 ± 0.2, 26.36 ± 0.2 | |
| | 14.77 ± 0.2, 20.87 ± 0.2, 21.76 ± 0.2, | |
| | 14.77 ± 0.2, 20.87 ± 0.2, 26.36 ± 0.2 | |
| | 14.77 ± 0.2, 21.76 ± 0.2, 26.36 ± 0.2 | |
| | 20.87 ± 0.2, 21.76 ± 0.2, 26.36 ± 0.2 | |
| | 14.77 ± 0.2, 20.87 ± 0.2, 21.76 ± 0.2, 26.36 ± 0.2 | |

In some embodiments, deuruxolitinib phosphate polymorph Form I has an XRPD pattern substantially as shown in FIG. 1.

In some embodiments, deuruxolitinib phosphate Form 1 can be determined by Differential Scanning Calorimetry (DSC) by determining the endotherm onset and peak of the polymorph. In some embodiments, the DSC spectrum can be determined at various rates, e.g., 2° C./min to 10° C./min, 4° C./min to 6° C./min, or 5° C./min. In some embodiments, the DSC spectrum can be determined at the rate of, e.g., 5° C./min to 30° C./min, 8° C./min to 15° C./min, or 10° C./min. In some embodiments, the DSC spectrum can be determined at the rate of, e.g., 30° C./min to 70° C./min, 40° C./min to 60° C./min, or 50° C./min.

In some embodiments, any of the DSC endotherm onset and/or peak temperatures described herein can be ±1.0° C. In some embodiments, any of the recited DSC endotherm onset and/or peak temperatures can be ±0.5° C., ±±0.2° C. or ±0.1° C. Thus, e.g., if deuruxolitinib phosphate Form 1 is described as having a DSC spectrum comprising an endotherm onset at 194.3±1.0° C. and peak at about 197.4° C. at 10° C./min. In some embodiments, deuruxolitinib phosphate Form 1 is described as having a DSC spectrum comprising an endotherm peak at 197.4±1.0° C., 197.4±0.5° C., 197.4±±0.2° C., 197.4±0.1° C. or 197.4° C., when determined at the rate of, e.g., 10° C./min.

In some embodiments, deuruxolitinib phosphate Form 1 is characterized by a DSC spectrum (10° C./min) comprising an endotherm peak at about 190.0±1.0° C. to about 200.0±1.0° C., about 195.0±1.0° C. to about 200.0±1.0° C., about 196.0±1.0° C. to about 198.0±1.0° C., or about 197.0±1.0° C. to about 198.0±1.0° C. In some embodiments, deuruxolitinib phosphate Form 1 is characterized by a DSC spectrum (10° C./min) comprising an endotherm peak at 197.4±1.0° C.

Figure 3:
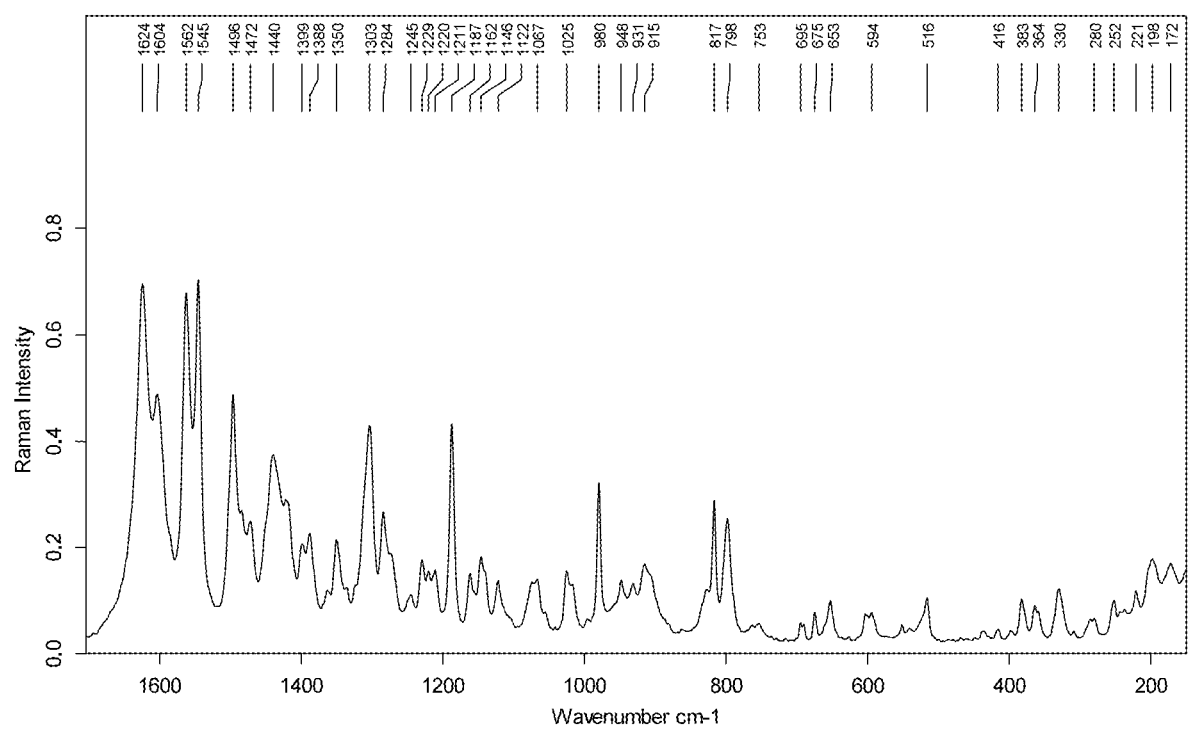
FIG. 3 depicts the FT-Raman spectrum of Form 1 of deuruxolitinib phosphate (1:1).

In some embodiments, deuruxolitinib phosphate Form 1 is characterized by a FT-Raman spectra having peaks at 4 or ore more, 5 or more, 6 or more or 7 or more of the following wave numbers ($cm^{-1}$): 1624, 1604, 1562, 1545, 1496, 1472, 1440, 1399, 1388, 1350, 1303, 1284, 1245, 1229, 1220, 1211, 1187, 1162, 1146, 1122, 1067, 1025, 980, 948, 931, 915, 817, 798, 753, 695, 675, 653, 594, 516, 416, 383, 364, 330, 280, 252, 221, 198 and 172. In some embodiments, deuruxolitinib phosphate Form 1 is characterized by a FT-Rama spectra as shown in FIG. 3.

Figure 4:
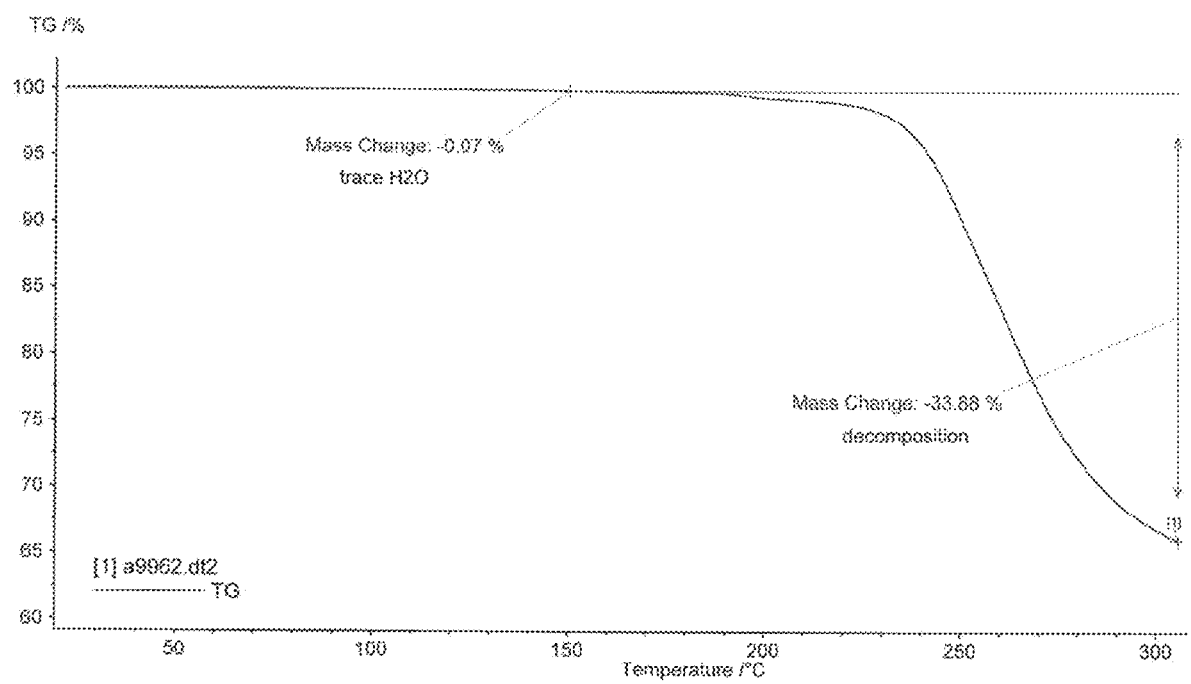
FIG. 4 depicts the TG-FTIR thermogram of Form 1 of deuruxolitinib phosphate (1:1).

In some embodiments, deuruxolitinib phosphate Form 1 is characterized by Thermogravimetric (TG) analysis. In some embodiments, the TG analysis is coupled to a spectroscopic method such as Fourier-Transform-Infrared (FT-IR) spectroscopy, i.e., TG-FTIR. In some embodiments, deuruxolitinib phosphate Form 1 is characterized by a TG-FTIR spectra as shown in FIG. 4.

In some embodiments, the deuruxolitinib phosphate Form 1 as described herein comprises at least 90% deuterium incorporation at each of the specified deuterated positions, as determined by $^{1}$H-NMR, e.g., at least 90% deuterium, at least 91% deuterium, at least 92% deuterium, at least 93% deuterium, at least 94% deuterium, at least 95% deuterium, at least 96% deuterium, at least 97% deuterium, at least 98% deuterium, or at least 99% deuterium incorporation.

In some embodiments, the deuruxolitinib phosphate Form 1 as described herein is substantially free of the (S) enantiomer of deuruxolitinib phosphate. Thus, in some embodiments, the deuruxolitinib phosphate Form 1 is less than 2%, less than 1.5%, less than 1%, less than 0.5%, less than ±0.2% or less than 0.1% (mol/mol) (S) enantiomer of deuruxolitinib phosphate. In some embodiments, the deuruxolitinib phosphate Form 1 is substantially free of 1H-pyrazole-1-propanenitrile, β-(cyclopentyl-2,2,3,3,4,4,5,5-$d_8$)-4-(7H-pyrrolo[2,3-d]pyrimidin-4-yl)-, (βS)-, phosphate (1:1) as determined by $^{1}$H-NMR.

In some embodiments, deuruxolitinib phosphate Form 1 is substantially free of amorphous 1H-pyrazole-1-propanenitrile, β-(cyclopentyl-2,2,3,3,4,4,5,5-$d_8$)-4-(7H-pyrrolo[2,3-$d_8$]pyrimidin-4-yl)-, (βR)-, phosphate (1:1). Thus, in some embodiments, the deuruxolitinib phosphate Form 1 is less than 2%, less than 1.5%, less than 1%, less than 0.5%, less than ±0.2% or less than 0.1% (wt/wt) amorphous deuruxolitinib phosphate.

In some embodiments, deuruxolitinib phosphate Form 1 is substantially free of any other polymorphic form of deuruxolitinib phosphate. Thus, in some embodiments, the deuruxolitinib phosphate Form 1 is less than 2%, less than 1.5%, less than 1%, less than 0.5%, less than ±0.2% or less than 0.1% (wt/wt) of any other polymorphic form of deuruxolitinib phosphate. In some embodiments, the ratio of the amount of Form 1 polymorph to the sum of the amounts of other polymorphic forms is at least 90:10 (wt/wt). In some embodiments, the ratio of the amount of Form 1 polymorph to the sum of the amounts of other polymorphic forms is at least 95:5 (wt/wt). In some embodiments, the ratio of the amount of Form 1 polymorph to the sum of the amounts of other polymorphic forms is at least 99:1 (wt/wt). In some embodiments, the ratio of the amount of Form 1 polymorph to the sum of the amounts of other polymorphic forms is at least 99.5:0.5 (wt/wt). In some embodiments, the ratio of the amount of Form 1 polymorph to the sum of the amounts of other polymorphic forms is at least 99.9:0.1 (wt/wt). In some embodiments, no other polymorphic forms are detected using standard techniques.

In some embodiments, the deuruxolitinib phosphate Form 1 is stable, i.e., the polymorphic form does not convert to another polymorphic form (or amorphous form) for a period of time when stored at room temperature. In some embodiments, the deuruxolitinib phosphate Form 1 is stable for at least 1 week, at least 1 month, at least 3 months, at least 6 months, at least 9 months, or at least 1 year when stored at room temperature. In some embodiments, the stability is determined by any methods known to the skilled articles, e.g., XRPD, DSC, FT-Raman spectroscopy and/or thermogravimetric measurements. In some embodiments, stability can be determined by looking at the XPRD spectra at T=0 and T=X, wherein X is the period of stability, wherein the polymorph form is considered stable if the method of polymorph determination, e.g., XPRD, DSC, FT-Raman spectroscopy and/or thermogravimetric measurements, produces a result, e.g., spectra, that does not substantially change over time as determined by the skilled artisan. In some embodiments, stability is determined using XPRD.

In some embodiments, the deuruxolitinib phosphate Form 1 is substantially anhydrous. Thus, in some embodiments, the deuruxolitinib phosphate Form 1 is less than 2%, less than 1.5%, less than 1%, less than 0.5%, less than 0.4%, less than 0.3%, less than ±0.2% less than 0.1%, less than 0.08%, less than 0.06% (wt/wt) of water as measured by Karl Fischer coulometric determination (USP 921). In some embodiments, the presence and amount of water is determined by TGA and/or by proton NMR analysis. In some embodiments, the deuruxolitinib phosphate Form 1 is substantially free of any solvent, e.g., is less than 2%, less than 1.5%, less than 1%, less than 0.5%, less than ±0.2% or less than 0.1% (wt/wt) of any solvent.

In some embodiments, the presence and amount of a solvent is determined by TGA and/or by proton NMR analysis. In some embodiments, the polymorph is substantially crystalline.

In some embodiments, the deuruxolitinib phosphate Form 1 comprises ≤10 ppm Cadmium (Cd), ≤5 ppm Cd, ≤2 ppm Cd, or ≤1 ppm Cd.

In some embodiments, the deuruxolitinib phosphate Form 1 comprises ≤10 ppm Lead (Pb), ≤5 ppm Pb, ≤2 ppm Pb, or ≤1 ppm Pb.

In some embodiments, the deuruxolitinib phosphate Form 1 comprises ≤10 ppm Arsenic (As), ≤5 ppm As, ≤2 ppm As, or ≤1 ppm As.

In some embodiments, the deuruxolitinib phosphate Form 1 comprises ≤10 ppm Mercury (Hg), ≤5 ppm Hg, ≤2 ppm Hg, or ≤1 ppm Hg.

In some embodiments, the deuruxolitinib phosphate Form 1 comprises ≤10 ppm Cobalt (Co), ≤5 ppm Co, ≤2 ppm Co, or ≤1 ppm Co.

In some embodiments, the deuruxolitinib phosphate Form 1 comprises ≤10 ppm Vanadium (V), ≤5 ppm V, ≤2 ppm V, or ≤1 ppm V.

In some embodiments, the deuruxolitinib phosphate Form 1 comprises ≤10 ppm Nickel (Ni), ≤5 ppm Ni, or ≤2 ppm Ni.

In some embodiments, the deuruxolitinib phosphate Form 1 comprises ≤250 ppm Rhodium (Ro), ≤200 ppm Ro, ≤100 ppm Ro, or ≤50 ppm Ro.

In some embodiments, the deuruxolitinib phosphate Form 1 is substantially enantiomerically pure. In some embodiments, the deuruxolitinib phosphate Form 1 comprises S-enantiomer not greater than 0.80% as determined by HPLC. In some embodiments, the deuruxolitinib phosphate Form 1 comprises S-enantiomer not greater than 0.70%, 0.60%, 0.50%, 0.40% or 0.30% as determined by HPLC.

In some embodiments, the deuruxolitinib phosphate Form 1 is substantially free of 4-(1H-pyrazol-4-yl)-7H-pyrrolo[2,3-d]pyrimidine, i.e., not greater than ±0.20% w/w (determined by HPLC). In some embodiments, the deuruxolitinib phosphate Form 1 comprises not greater than 0.10% or 0.05% w/w 4-(1H-pyrazol-4-yl)-7H-pyrrolo[2,3-d]pyrimidine as determined by HPLC.

In some embodiments, the deuruxolitinib phosphate Form 1 is substantially free of impurities as determined by HPLC. In some embodiments, the deuruxolitinib phosphate Form 1 comprises not more than 2.0%, not more than 1.0% or not more than 0.5% (w/w) total impurities as measured by HPLC.

In some embodiments, the deuruxolitinib phosphate Form 1 is suitable for use in a pharmaceutical composition. In some embodiments, the disclosure provides for a pharmaceutical composition comprising the deuruxolitinib phosphate Form 1 and a pharmaceutically acceptable carrier. In some embodiments, the term "pharmaceutically acceptable" refers to a substance that is suitable for use in humans and/or animals without excessive adverse side effects (such as toxicity, irritation, and allergies), that is, with a reasonable benefit/risk ratio.

In some embodiments, the disclosure provides a unit dose form comprising deuruxolitinib phosphate Form 1, in an amount in the range of about 4 mg to about 50 mg (for example, about 5 mg, about 10 mg, about 20 mg, about 30 mg, about 40 mg, or about 50 mg), free base equivalent, together with a pharmaceutically acceptable carrier or diluent. In certain embodiments, the amount of deuruxolitinib phosphate Form 1 is about 4 mg, 8 mg, 16 mg, 24 mg, 32 mg or 48 mg. In certain embodiments, the amount of deuruxolitinib phosphate Form 1 is 4 mg, 8 mg, 12 mg, or 16 mg (free base equivalent). In certain embodiments, the amount of deuruxolitinib phosphate Form 1, is 5.3 mg. In certain embodiments, the amount of deuruxolitinib phosphate Form 1 is 10.5 or 10.6 mg. In certain embodiments, the amount of deuruxolitinib phosphate Form 1 is 15.8 mg. In certain embodiments, the amount of deuruxolitinib phosphate Form 1 is 21.1 mg. In certain embodiments, the unit dose form is a tablet or capsule.

In some embodiments, the pharmaceutical compositions as described herein can comprise other therapeutically active substances.

In some embodiments, the pharmaceutical composition of the present disclosure is formulated for parenteral administration, including formulated for oral, intravenous, topical, or transdermal administration. In some embodiments, pharmaceutical composition of the present disclosure is formulated for oral delivery. In some embodiments, the pharmaceutical composition comprising the deuruxolitinib phosphate Form 1 described herein is formulated in the form of a pill, tablet, capsule, syrup, lozenge, or liquid formulation. Formulations for pills, tablets, and hard gelatin capsules can comprise additional excipients known to the skilled artisan.

In some embodiments, the pharmaceutical compositions comprising the deuruxolitinib phosphate Form 1 described herein are in a dosage form suitable for treatment of a diseases, disorders or conditions.

In some embodiments, the disclosure provides methods for treatment of diseases, disorders or conditions mediated alone, or in part, by Janus Associated Kinases (JAKs). In one embodiment, the disclosure comprises administering an effective amount of deuruxolitinib phosphate Form 1 to a subject in need thereof.

The term "disease, disorder or condition mediated alone, or in part, by Janus Associated Kinases (JAKs)" refers to a disease, condition, or disorder that can be treated by compounds that modulate the activity of Janus Associated Kinase 1 (JAK1) and/or Janus Associated Kinase 2 (JAK2). Such diseases, conditions or disorders include, without limitation, skin diseases such as proliferative, autoimmune and/or inflammatory skin disorders including psoriasis, atopic dermatitis, scleroderma, rosacea, skin cancers, dermatitis, dermatitis herpetiformis, dermatomyositis, vitiligo, hair loss disorders, contact dermatitis, xerosis, ichthyosis, hidradenitis suppurativa, urticaria, lichen planus, prurigo nodularis, vasculitis, cutaneous lupus erythematosus (CLE), and chronic idiopathic pruritus; hyperproliferative disorders or cancers including polycythemia vera, essential thrombocytopenia, and myelofibrosis; respiratory diseases such as asthma, chronic obstructive pulmonary disease, chronic lung allograft dysfunction, e.g., bronchiolitis obliterans syndrome, pulmonary fibrosis, cystic fibrosis, rhinitis, bronchiolitis, byssinosis, pneumoconiosis, bronchiectasis, hypersensitivity pneumonitis, lung cancers, mesothelioma and sarcoidosis; gastrointestinal diseases such as inflammatory bowel disease, ulcerative colitis, Crohn's disease, retroperitoneal fibrosis, celiac disease and cancers; eye diseases such as myasthenia gravis, Sjogren's syndrome, conjunctivitis, scleritis, uveitis, dry eye syndrome, keratitis, iritis; systemic indications such as lupus, multiple sclerosis, rheumatoid arthritis, type I diabetes and complications from diabetes, cancers, ankylosing spondylitis and psoriatic arthritis; as well as other autoimmune diseases and indications where immunosuppression would be desirable, for example, to treat or prevent acute and/or chronic graft-versus-host disease (e.g., in organ transplantation). In certain embodiments, a disease or condition mediated alone, or in part, by Janus Associated Kinases (JAKs) is a hair loss disorder, such as alopecia areata.

In certain embodiments, the Form 1 of deuruxolitinib phosphate is administered in an amount in the range of about 2 mg to about 48 mg per day (free base equivalent weight). In certain embodiments, the Form 1 of deuruxolitinib phosphate is administered in an amount in the range of about 8 mg to about 32 mg per day (free base equivalent weight). In certain embodiments, the Form 1 of deuruxolitinib phosphate is administered at about 8 mg/day, about 12 mg/day, about 16 mg/day, about 24 mg/day, or about 32 mg per day (free base equivalent weight). In some embodiments, Form 1 of deuruxolitinib phosphate is administered in an amount in the range of about 4 mg to about 50 mg (for example, about 5 mg, about 10 mg, about 20 mg, about 30 mg, about 40 mg, or about 50 mg), free base equivalent, together with a pharmaceutically acceptable carrier or diluent. In certain embodiments, the amount of deuruxolitinib phosphate Form 1 administered per day is about 4 mg, 8 mg, 16 mg, 24 mg, 32 mg or 48 mg. In certain embodiments, the amount of deuruxolitinib phosphate Form 1 administered at one time is 4 mg, 8 mg, 12 mg, or 16 mg (free base equivalent). In certain embodiments, the amount of deuruxolitinib phosphate Form 1 administered per day is 5.3 mg. In certain embodiments, the amount of deuruxolitinib phosphate Form 1 administered per day is 10.5 or 10.6 mg. In certain embodiments, the amount of deuruxolitinib phosphate Form 1 administered per day is 15.8 mg. In certain embodiments, the amount of deuruxolitinib phosphate Form 1 administered per day is 21.1 mg. In certain embodiments, the deuruxolitinib phosphate Form 1 is administered in a unit dose form, e.g., an oral unit dose for, e.g., a tablet or capsule.

In some embodiments, the disclosure provides a method of preparing deuruxolitinib phosphate Form 1. In some embodiments, the process comprises forming a slurry of deuruxolitinib phosphate with a solvent, e.g., a $C_2$-$C_4$ alcohol, or a mixture of two solvents, e.g., a $C_2$-$C_4$ alcohol and a co-solvent, e.g., water. In some embodiments, the $C_2$-$C_4$ alcohol is ethanol, propanol, or isopropanol. In some embodiments, the process comprises forming a slurry of deuruxolitinib phosphate with isopropanol and water. In some embodiments, the process comprises forming a slurry of deuruxolitinib phosphate with isopropanol. In some embodiments, the process comprises forming a slurry of deuruxolitinib phosphate with ethanol.

In some embodiments, the slurry is formed in an isopropanol/water mixture at a ratio of about 10:90 to about 90:10, about 30:70 to about 70:30, or about 50:50. In some embodiments, the slurry is formed in an isopropanol/water mixture at a ratio of about 80:20 to about 98:2, about 85:15 to about 95:5, about 88:12 to about 92:8, or about 90:10. In some embodiments, the slurry is formed in an isopropanol/water mixture at a ratio of about 90:10. In some embodiments, the slurry is formed at a temperature of about 5° C. to about 30° C., or about 15° C. to about 25° C. In some embodiments, the slurry is mixed for about 10 minutes to about 24 hours, about 20 minutes to about 12 hours, or about 1 hour to about 6 hours.

In some embodiments, the slurry is formed wherein the solvent is isopropanol. In some embodiments when the solvent is isopropanol, the slurry is formed at a temperature of about 20° C. to about 90° C., about 50° C. to about 75° C., or about 70° C.

In some embodiments, the slurry is formed wherein the solvent is ethanol. In some embodiments when the solvent is ethanol, the slurry is formed at a temperature of about 20° C. to about 90° C., about 50° C. to about 75° C., or about 70° C. In some embodiments, the pH is adjusted to about 3 to about 7, or about 4 to about 5.

In some embodiments, the deuruxolitinib phosphate is dissolved in a solvent at 20° C. to 70° C. to form a solution. In some embodiments, this can be referred to as a "dissolving temperature." In some embodiments, the deuruxolitinib phosphate is dissolved in a solvent at 25° C., 30° C., 35° C., 40° C., 45° C., or 50° C. to 70° C. to form a solution. In some embodiments, deuruxolitinib phosphate is dissolved in a solvent at 25° C. to 30° C., 30° C. to 35° C., 35° C. to 40° C., 40° C. to 45° C., or 45° C. to 50° C., 50° C. to 60° C., 60° C. to 70° C., or 70° C. to 80° C. to form a solution.

In some embodiments, the deuruxolitinib phosphate dissolved in the solution is less than 10% (wt/vol), less than 5% (wt/vol), less than 4% (wt/vol), or less than 3% (wt/vol) of the solvent. In some embodiments, the concentration of deuruxolitinib phosphate is less than the saturation point for a given solvent and temperature, e.g., if the saturation point of deuruxolitinib phosphate for a given solvent and temperature is "X mg/mL," then the concentration of deuruxolitinib phosphate is less than "X mg/mL", e.g., 20% less, 50% less, or 80% less.

In some embodiments, the deuruxolitinib phosphate dissolved in the solvent forms a solution, wherein the solution is cooled to an incubation temperature. In some embodiments, the incubation temperature is held for a "period of time." In some embodiments, the period of time is greater than 1 hour, greater than 2 hours, greater than 3 hours, greater than 4 hours, greater than 5 hours, greater than 6 hours, greater than 8 hours, greater than 10 hours, greater than 12 hours, greater than 15 hours, greater than 20 hours, greater than 24 hours, greater than 2 days, or greater than 3 days. In some embodiments, the period of time for the incubation temperature is about 1 hours to about 48 hours, about 2 hours to about 36 hours, about 3 hours to about 24 hours, about 4 hours to about 20 hours, or about 6 hours to about 18 hours. In some embodiments, the incubation temperature is about 1° C. to about 10° C. for a period of time. In some embodiments, the incubation temperature is about 2° C. to about 8° C., about 3° C. to about 7° C., or about 4° C. to about 6° C. for a period of time.

In some embodiments, the deuruxolitinib phosphate is mixed with the solvent to form a slurry, wherein the slurry is mixed for about 2 hours to about 12 hours, about 3 hours to about 8 hours, or about 4 hours to about 7 hours. In some embodiments, the slurry is mixed for greater than 4 hours, greater than 5 hours, or greater than 6 hours.

In some embodiments, the change of temperature from the dissolving temperature to the incubation temperature can be done over a defined time period, i.e., a rate of change or temperature over the given time. In some embodiments, the cooling from the dissolving temperature to the incubation temperature is at a rate of about 0.02° C./min to about 1° C./min until the incubation temperature is reached. In some embodiments, the cooling to the incubation temperature is at a rate of about 0.05° C./min to about 0.5° C./min until the incubation temperature is reached. In some embodiments, the cooling to the incubation temperature is at a rate of about 0.1° C./min to about 0.3° C./min until the incubation temperature is reached.

In some embodiments, after the incubation temperature is held for a period of time, the solvent is then removed and the deuruxolitinib phosphate crystalizes. In some embodiments, the crystallization process can be initiated using seed crystals or other initiating composition. In some embodiments, the solvent is removed and the polymorphs form over a specified time, i.e., the removal time. One of skill in the art will appreciate that as the concentration of solvent is decreased, the concentration of deuruxolitinib phosphate will increase until the crystallization process initiates. The skilled artisan will also appreciate that a number of factors may affect the removal time, e.g., the amount of solvent to be removed, the type of solvent being removed, the temperature, the pressure, etc., will affect the removal time of the solvent.

In some embodiments, the particle form in the slurry without the need for an incubation period, i.e., the particles can be isolated immediately after mixing is complete.

In some embodiments, the solvent is removed by evaporation. The skilled artisan will appreciate that the rate of evaporation will be determined by a number of factors, including, but not limited to the identity of the solvent, the temperature, the pressure, etc. In some embodiments, the evaporation is performed at the incubation temperature. In some embodiments, the evaporation temperature can vary, e.g., can vary over time. In some embodiments, the evaporation temperature is constant. In some embodiments, the evaporation is performed at a temperature greater than the incubation temperature. In some embodiments, the evaporation is performed at greater than 5° C., greater than 10° C., greater than 15° C., greater than 20° C., greater than 25° C., or greater than 30° C. In some embodiments, the evaporation is performed at 5° C. to 40° C., 10° C. to 35° C., 15° C. to 30° C. In some embodiments, the evaporation is performed at about 20° C. to about 35° C. In some embodiments, if more than one solvent is present, the evaporation temperature can be maintained at a first temperature until the first solvent is evaporated, and then changed to a second temperature. In some embodiments, the evaporation can be performed at various temperatures. In some embodiments, the evaporation is performed at 1 atmosphere pressure. In some embodiments, the evaporation is performed at less than 1 atmosphere pressure.

In some embodiments, the removing of the solvent is performed by filtration. For example, in some embodiments, the solvent is removed using a membrane or semi-permeable membrane. In some embodiments, when using the semi-permeable membrane, the solvent is replaced by a different solvent, wherein the deuruxolitinib phosphate forms crystals in the different solvent. In some embodiments, the filter has a pore size of less than 50 μm, less than 30 μm, or less than 25 μm. In some embodiments, the filter has a pore size of 22 μm. Various filters are known in the art. In some embodiments, the filter I nonreactive with the polymorph.

In some embodiments, the filter is a hydrophobic filter. In some embodiments, the filter is a polytetrafluoroethylene (PTFE) filter, e.g., a PTFE filter with a pore size of 22 μm.

In some embodiments, the solvent is removed by lyophilization.

In some embodiments, the deuruxolitinib phosphate Form 1 is isolated from the slurry via filtration. In some embodiments, the disclosure provides for a process for the preparation of deuruxolitinib phosphate Form 1 as described herein, wherein the method comprises (i) forming a slurry of 1H-pyrazole-1-propanenitrile, β-(cyclopentyl-2,2,3,3,4,4,5,5-ds)-4-(7H-pyrrolo[2,3-d]pyrimidin-4-yl)-, (βR)-, phosphate (1:1) in isopropanol or an isopropanol/water mixture, and (ii) isolating Form 1 of deuruxolitinib phosphate from the slurry by filtration.

Examples

Synthesis of 1H-pyrazole-1-propanenitrile, β-(cyclopentyl-2,2,3,3,4,4,5,5-d$_8$)-4-(7H-pyrrolo[2,3-d]pyrimidin-4-yl)-, (βR)-, phosphate (1:1) Form 1

A) To 49.3 mg of deuruxolitinib phosphate was added 2.0 ml of a 2-propanol-water 9:1 solution resulting in a suspension that was agitated at 600 rpm at ambient temperature for ~3 days. The suspension was then filtered (±0.22 μm, PTFE) resulting in a white polycrystalline powder—XRPD matches with Form 1.

B) To 55.9 mg deuruxolitinib phosphate was added 3.0 ml 2-propanol resulting in a suspension that was agitated at 70° C. and 600 rpm for 6 days. The suspension was then filtered (±0.22 μm, PTFE) resulting in a white polycrystalline powder—XRPD matches with Form 1.

C) To a solution of 100.6 mg deuruxolitinib as the free base in 1.0 ml EtOH was added while stirring vigorously, 15.2 μl (0.5 equivalents) phosphoric acid (85% aqueous solution). Precipitation to a very thick slurry took place within seconds. An extra 1.0 ml EtOH was added to keep the slurry mobile. After the slurry was stirred for a further 2 days at ambient temperature, solid was isolated by centrifuge filtration and dried in the vacuum oven at ambient temperature. The pH of the mother liquor was measured as 4.66. The resulting solid was analyzed by XRPD and Raman and corresponded to Form 1.

D) Step 1: A solution in isopropanol of wet deuruxolitinib phosphate was transferred into a reactor through a cartridge filter and was stirred at 20-25° C. for 5 minutes before IPC analysis was done to determine the concentration of deuruxolitinib phosphate. Concentration was adjusted to fall between >70 mg/ml and <100 mg/ml by concentrating under vacuum at ≤84° C. or by adding isopropanol. The mixture was thermoregulated at 60-65° C. and a portion of "acidic solution of isopropanol for wet deuruxolitinib phosphate" was added according to the following formulas:

Formula I: kg of $H_3PO_4$ (85%) to be added=[total weight of measured "solution in isopropanol of wet deuruxolitinib phosphate"×concentration of deuruxolitinib phosphate/100]×0.39.

Formula II: "Acidic solution of isopropanol for wet deuruxolitinib phosphate" to be loaded=(total weight of "acidic solution of isopropanol for wet deuruxolitinib phosphate"/the quantity of $H_3PO_4$ (85%) loaded to prepare the acidic solution of isopropanol×result of Formula I.

Step 2: The wet product was dried under vacuum at 45° C. for 16 hours. The dry product was discharged from the drier and sieved with a 1.0 mm sieve to provide deuruxolitinib phosphate Form 1.

The resulting particles from Examples A), B), C), and/or D) were then subjected to XPRD, Thermal Analysis, FT-RAMAN, and TG-FTIR as described below and corresponded to deuruxolitinib phosphate Form 1.

XRPD

X-ray powder diffraction (XRPD) data were obtained using a Stoe Stadi P equipped with a Mythen1K Detector; Cu-Kα1 radiation; standard measurement conditions: transmission; 40 kV and 40 mA tube power; curved Ge monochromator; 0.02°2θ step size, 48s step time, 1.5-50.5°2θ scanning range; detector mode: step scan; 1°2θ detector step. The samples (10-20 mg of powder) were measured between two acetate foils or Kapton foils. No special treatment was used in preparing the samples other than the application of slight pressure to distribute the powder over the irradiated surface area. An ambient air atmosphere was used for all measurements, and each sample was rotated during the measurement.

Using the above conditions, 2-theta Peak Values and intensities of deuruxolitinib phosphate Form 1 (Example D) were determined as found in Table 3.

TABLE 3

| Peak (2Θ) | Intensity [cts] |
|---|---|
| 4.03 | 5896 |
| 14.54 | 3091 |
| 24.95 | 2111 |
| 25.29 | 2196 |
| 14.77 | 977 |
| 20.87 | 1293 |
| 21.76 | 1551 |
| 26.36 | 1821 |

TABLE 3-continued

| Peak (2Θ) | Intensity [cts] |
|---|---|
| 7.55 | 369 |
| 8.36 | 377 |
| 15.94 | 905 |
| 20.41 | 861 |

The complete XPRD of deuruxolitinib phosphate Form 1 is found in FIG. 1.

Thermal Analysis

Differential scanning calorimetry (DSC) thermograms of the particles were recorded on a TA Instruments Q2000 instrument. The closed (hermetically sealed) gold or aluminum sample pans were filled with sample under ambient conditions. The measurements were conducted with a heating rate of 10° C./min. The melting point is understood as the peak maximum.

Figure 2:
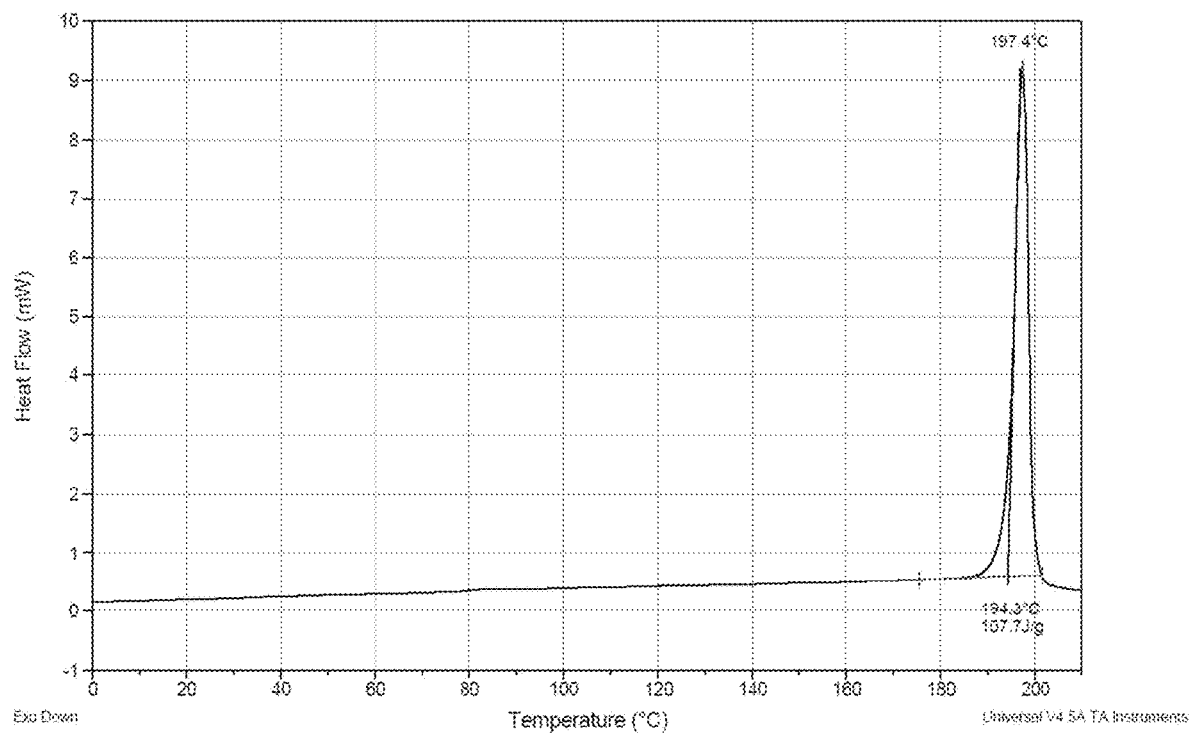
FIG. 2 depicts the differential scanning calorimetry (DSC) thermogram of Form 1 of deuruxolitinib phosphate (1:1).

The DSC of deuruxolitinib phosphate Form 1 was determined to be 197.4±1.0° C. as is found in FIG. 2

FT-Raman

FT-Raman spectra were recorded on a Bruker MultiRAM FT-Raman system with a near infrared Nd:YAG laser operating at 1064 nm and a liquid nitrogen-cooled germanium detector. 64 scans with a resolution of 2 cm$^{-1}$ were accumulated in the range from 3500 to −50 cm$^{-1}$; however, only data above 100 cm$^{-1}$ are evaluated due to filter cutoff effects. Nominal laser powers are typically 100 or 300 mW.

The FT-Raman spectra of deuruxolitinib phosphate Form 1 is found in FIG. 3.

TG-FTIR

Thermogravimetric measurements were carried out with a Netzsch Thermo-Microbalance TG 209 coupled to a Bruker FT-IR Spectrometer Vector 22. Aluminum sample pans with a pinhole or hermetic gold pans, N$_2$ atmosphere, heating rate 10° C./min.

TG-FTIR spectra of deuruxolitinib phosphate Form 1 is found in FIG. 4.

I claim:

1. A polymorph of a compound of Formula I:

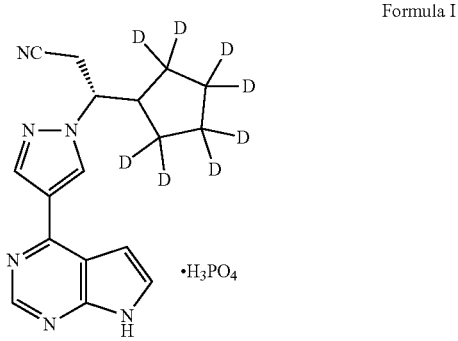

Formula I wherein the polymorph is Form I; and
wherein Form I is characterized by a powder X-ray diffraction pattern comprising at least three peaks at angles (°2θ) selected from 4.03°±0.2°2θ, 14.54°±0.2°2θ, 24.95°±0.2°2θ, and 25.29°±0.2°2θ.

2. The polymorph of claim 1, wherein the polymorph is further characterized by a powder X-ray diffraction pattern comprising peaks at angles (°2θ) of 4.03°±0.2°2θ, 14.54°±0.2°2θ, 24.95°±0.2°2θ, and 25.29°±0.2°2θ.

3. The polymorph of claim 2, wherein the polymorph is further characterized by a powder X-ray diffraction pattern comprising at least one additional peak at an angle (°2θ) selected from 14.77°±0.2°2θ, 20.87°±0.2°2θ, 21.76°±0.2°2θ, and 26.36°±0.2°2θ.

4. The polymorph of claim 2, wherein the polymorph is further characterized by a powder X-ray diffraction pattern comprising at least two additional peaks at angles (°2θ) selected from 14.77°±0.2°2θ, 20.87°±0.2°2θ, 21.76°±0.2°2θ, and 26.36°±0.2°2θ.

5. The polymorph of claim 2, wherein the polymorph is further characterized by a powder X-ray diffraction pattern comprising at least three additional peaks at angles (°2θ) selected from 14.77°±0.2°2θ, 20.87°±0.2°2θ, 21.76°±0.2°2θ, and 26.36°±0.2°2θ.

6. The polymorph of claim 2, wherein the polymorph is further characterized by a powder X-ray diffraction pattern comprising four additional peaks at angles (°2θ) of 14.77°±0.2°2θ, 20.87°±0.2°2θ, 21.76°±0.2°2θ, and 26.36°±0.2°2θ.

7. The polymorph of claim 1, wherein the polymorph is further characterized by a powder X-ray diffraction pattern comprising at least one additional peak at an angle (°2θ) selected from 7.55°±0.2°2θ, 8.36°±0.2°2θ, 15.94°±0.2°2θ, and 20.41°±0.2°2θ.

8. The polymorph of claim 1, wherein the polymorph is further characterized by a powder X-ray diffraction pattern comprising at least two additional peaks at angles (°2θ) selected from 7.55°±0.2°2θ, 8.360°±0.2°2θ, 15.940°±0.2°2θ, and 20.41°±0.2°2θ.

9. The polymorph of claim 1, wherein the polymorph is further characterized by a powder X-ray diffraction pattern comprising at least three additional peaks at angles (°2θ) selected from 7.55°±0.2°2θ, 8.360°±0.2°2θ, 15.94°±0.2°2θ, and 20.41°±0.2°2θ.

10. The polymorph of claim 1, wherein the polymorph is further characterized by a powder X-ray diffraction pattern as shown in FIG. 1.

11. The polymorph of claim 1, wherein the polymorph is further characterized by at least one of (a), (b), and (c):
    (a) a differential scanning calorimetry (DSC) spectrum (10° C./min) comprising an endotherm onset at 194.3° C.±1.0° C. and peak at 197.4° C.±1.0° C.;
    (b) a Fourier transform (FT)-Raman spectrum as depicted in FIG. 3; and
    (c) a thermogravimetric-Fourier transform infrared (TG-FTIR) thermogram as depicted in FIG. 4.

12. The polymorph of claim 11, wherein the polymorph Is further characterized by at least 90% deuterium incorporation at each of the specified deuterated positions, as determined by $^1$H-NMR.

13. The polymorph of claim 11, wherein the polymorph Is further characterized by at least 95% deuterium incorporation at each of the specified deuterated positions, as determined by $^1$H-NMR.

14. A pharmaceutical composition comprising the polymorph of claim 1 and a pharmaceutically acceptable carrier.

* * * * *